US007754823B2

(12) United States Patent  (10) Patent No.: US 7,754,823 B2
Binder et al.  (45) Date of Patent: Jul. 13, 2010

(54) VEGETABLE BASED DIOXANONE DERIVATIVES, SYNTHESIS AND USES THEREOF

(75) Inventors: Thomas Paul Binder, Decatur, IL (US); Paul David Bloom, Decatur, IL (US)

(73) Assignee: Archer-Daniels-Midland Company, Decatur, IL (US)

(*) Notice: Subject to any disclaimer, the term of this patent is extended or adjusted under 35 U.S.C. 154(b) by 1511 days.

(21) Appl. No.: 11/087,772

(22) Filed: Mar. 24, 2005

(65) Prior Publication Data

US 2005/0234121 A1   Oct. 20, 2005

Related U.S. Application Data

(60) Provisional application No. 60/555,702, filed on Mar. 24, 2004.

(51) Int. Cl.
*C08G 63/91* (2006.01)
(52) U.S. Cl. .................... 525/415; 528/73; 514/452; 514/547
(58) Field of Classification Search ................. 525/415; 528/73, 81; 260/535; 514/452, 547
See application file for complete search history.

(56) References Cited

U.S. PATENT DOCUMENTS

| | | | |
|---|---|---|---|
| 3,210,325 A | 10/1965 | De Witt et al. | |
| 3,280,065 A | 10/1966 | Langner | |
| 3,341,458 A | 9/1967 | Mayhew et al. | |
| 3,929,846 A | 12/1975 | Snapp, Jr. et al. | |
| 3,929,847 A | 12/1975 | Snapp, Jr. et al. | |
| 3,970,619 A | 7/1976 | Snapp, Jr. et al. | |
| 4,002,676 A * | 1/1977 | Borggrefe | 562/583 |
| 4,201,216 A * | 5/1980 | Mattei | 606/230 |
| 4,525,288 A | 6/1985 | Schlicht | |
| 5,371,176 A | 12/1994 | Bezwada et al. | |
| 5,717,059 A | 2/1998 | Forschner | |
| 5,868,788 A | 2/1999 | Bezwada et al. | |
| 6,083,524 A | 7/2000 | Sawhney et al. | |
| 6,339,130 B1 * | 1/2002 | Bennett et al. | 525/415 |
| 6,548,609 B2 | 4/2003 | Ramírez-de-Arellano-Aburto et al. | |
| 6,924,333 B2 | 8/2005 | Bloom et al. | |
| 2006/0020062 A1 | 1/2006 | Bloom | |

FOREIGN PATENT DOCUMENTS

| | | |
|---|---|---|
| CA | 1260488 A1 | 9/1989 |
| DE | 1 054 444 B | 4/1959 |
| DE | 195 42 933 A1 | 5/1997 |

OTHER PUBLICATIONS

USPTO STIC structure search Sep. 18, 2008.*
Friedrich, J.P., "Low-Pressure Hydroformylation of Methyl Oleate with an Activated Rhodium Catalyst," *Ind. Eng. Chem. Prod. Res. Dev.* 17:205-207, American Chemical Society (1978).
Rao, G. Venkateswara, "Protection of Unsaturation by Cupric Nitrate During Heterogeneous Catalytic Hydrogenation of Aliphatic Epoxy to Hydroxy Groups," *J. Am. Oil Chem. Soc.* 45:408, American Oil Chemists Society (1968).
Database Caplus, Accession No. 1974:505413, English language abstract for Stoilov, L. and Iovchev, A., "Replacement of the double bond of monoenic fatty acids by the 1,4-dioxane ring," *Doklady Bolgarskoi Akademii Nauk* 26:1355-1357 (1973), Chemical Abstracts Service (1973).
Database Caplus, Accession No. 1976:105922, English language abstract for Kochetkov et al., "New sugars from the antigenic lipopolysaccharides of *Shigella*," *Biiorganicheskaya Khimiya* 1:1238-1240 (1975), Chemical Abstracts Service (1976).
Database Caplus, Accession No. 1981:498186, English language abstract for Orosco, L.R. and Chizhov, O.S., "Glucolactylic acids. III. Synthesis of 2-O-[(S)-1-carboxyethyl]-D-glucose and its R-isomer," *Bioorganicheskaya Khimiya* 7:741-749 (1981), Chemical Abstracts Service (1981).
Osman, S.F. and Fett, W.F., "Structure of the acidic exopolysaccharide of *Pseudomonas marginalis* Strains ATCC 10844," *Carbohydrate Research* 242:271-275 (1993).
Oxley, D. and Wilkinson, S.G., "Structure of an acidic glycan present in the lipopolysaccharide extract from the reference strain for *Serratia marcescens* serogroup O18," *Carbohydrate Research* 215:293-301 (1991).
Partial International Search Report for International Patent Application No. PCT/US2005/009968, 5 pages, European Patent Office, The Hague, Netherlands, mailed Sep. 1, 2005.
Partial English Language Translation for German Patent, DE 10 54 444 B (Document FP1, listed on form PTO/SB/08A of First Supplemental Information Disclosure Statement previously submitted on Jan. 4, 2006).
English Language Translation for German Patent, DE 195 42 933 A1(Document FP3, listed on form PTO/SB/08A of First Supplemental Information Disclosure Statement previously submitted on Jan. 4, 2006).

* cited by examiner

*Primary Examiner*—James Seidleck
*Assistant Examiner*—Gregory Listvoyb
(74) *Attorney, Agent, or Firm*—Sterne, Kessler, Goldstein & Fox P.L.L.C.

(57) ABSTRACT

The present invention is directed to carboxylic acid and ester moieties that are attached to a carbon chain that is between 2 and 24 carbons in length wherein, the chain contains at least one dioxanone ring system, said dioxanone being formed from two adjacent carbons in the chain and/or at least one carbon in the chain is substituted with a pendant dioxanone ring system. In preferred embodiments, the carbon chain is a fatty acid residue. The carbons of said chain can be optionally substituted, saturated or unsaturated. When two or more said ester moieties are present, the invention is directed to a polyester such as a triglyceride, that contains multiple carbon chains wherein each chain is independently derivatized such that the triglyceride contains at least one dioxanone ring system, said dioxanone being formed from two adjacent carbons in at least one of said chains. The present invention is also directed to a method of preparing a dioxanone containing composition or fatty acid derivative. The present invention is also directed to coating formulations and polymers that utilize a dioxanone containing composition or fatty acid derivative, and methods of making such coatings and polymers.

16 Claims, No Drawings

VEGETABLE BASED DIOXANONE DERIVATIVES, SYNTHESIS AND USES THEREOF

CROSS REFERENCE TO RELATED APPLICATIONS

This application claims benefit under 35 U.S.C. §119(e) to U.S. Provisional Application: 60/555,702 filed Mar. 24, 2004, hereby incorporated herein by reference.

BACKGROUND OF THE INVENTION

Field of the Invention

In the past, fatty acid based chemicals have been functionalized with petrochemical based materials to make new industrial derivatives. Current efforts still are underway to expand the functionality of vegetable oil products with petrochemical feedstocks, such as phenol. In order to produce more sustainable new industrial chemicals, biobased components of new chemicals should be increased. Dioxanone derivatives of fatty acid dervatives are based substantially on ethyl lactate and vegetable oils, which are both derived from biobased sources.

BRIEF SUMMARY OF THE INVENTION

The present invention is directed to compounds and compositions containing carboxylic acid and/or ester moieties that are attached to a carbon chain that is 2 to 23 carbons in length, wherein the chain contains at least one dioxanone ring system, the dioxanone being formed from two adjacent carbons in the chain. The present invention is also directed to compounds and compositions containing carboxylic acid and/or ester moieties that are attached to a carbon chain that is 2 to 23 carbons in length, wherein the chain is substituted with at least one dioxanone ring system. In preferred embodiments, the carbon chain is a fatty acid residue. The carbons of the chain can be optionally substituted, saturated or unsaturated. When two or more ester moieties are present, the invention is directed to a polyol polyester such as a triglyceride, that contains multiple carbon chains wherein each chain is independently derivatized such that the triglyceride contains at least one dioxanone ring system, with the dioxanone being formed from two adjacent carbons in at least one of said chains, or at least one dioxanone ring system is present as a substituent on at least one of the chains. The present invention is also directed to a method of preparing a dioxanone containing composition or fatty acid derivative. The present invention is also directed to coating formulations and polymers that utilize a dioxanone containing composition or fatty acid derivative, and methods of making such coatings and polymers.

DETAILED DESCRIPTION OF THE INVENTION

The present invention is directed to compositions and fatty acid derivatives that contain a carbon chain that is 2 to 24 carbons in length, wherein the chain contains at least one dioxanone ring system such that two adjacent carbons in the chain of the fatty acid derivative are embedded in the dioxanone ring system as shown in the following general structure (I):

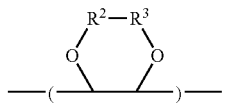

wherein one of $R^2$ and $R^3$ is a carbonyl and the other of $R^2$ and $R^3$ is $CR_4R_5$, wherein $R_4$ and $R_5$ are independently selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl and phenyl($C_{1-4}$)alkyl. The present invention is also directed to fatty acid derivatives that contain a carbon chain that is 2 to 24 carbons in length, where at least one carbon in the chain is substituted with a dioxanone ring system. This substituent can be referred to as a pendant dioxanone ring system.

In one embodiment, the present invention is directed to a composition comprising a carboxyl moiety attached to a carbon chain that is between 2 and 23 carbons in length, wherein the chain contains at least one dioxanone ring system, the dioxanone being formed from two adjacent carbons in the chain and having the general structure (I) shown above. In this embodiment, the composition has the following general structure:

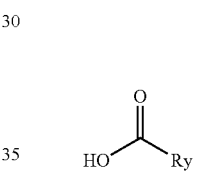

wherein $R_y$ is a carbon chain 2 to 23 carbons in length and is optionally substituted, saturated or unsaturated, and wherein the chain contains at least one dioxanone ring system.

In this embodiment, the carbons of the carbon chain are independently substituted with one or more substituents selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl and phenyl($C_{1-4}$)alkyl. Further, the chain can be functionalized to include an optionally substituted or unsubstituted dioxanone ring system or other groups as described herein as a substituent. These pendant dioxanone ring systems can be illustrated by a functionalized derivative of linoleic acid (cis, cis-9,12-octadecadienoic acid):

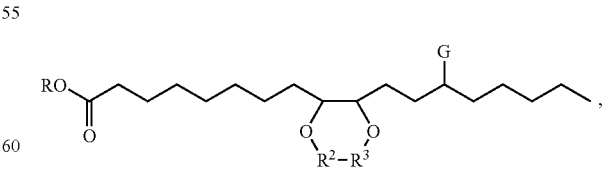

wherein, R can be H or $C_{1-4}$ alkyl; $R^2$ and $R^3$ are as described above; and G can be a dioxanone substituent on the chain, wherein the dioxanone moeity has one of the following structures, $G^1$ and $G^2$, or alternatively $G^3$, $G^4$, $G^5$, $G^6$, and $G^7$:

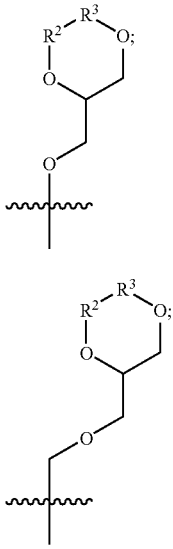

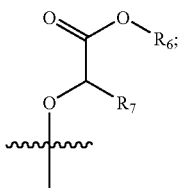

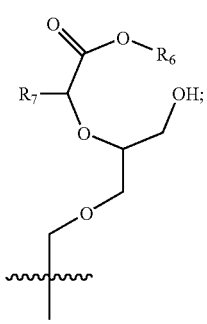

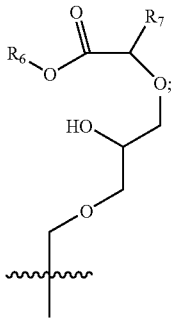

wherein one of $R^2$ and $R^3$ is a carbonyl and the other of $R^2$ and $R^3$ is $CR_4R_5$, and wherein $R_4$ and $R_5$ are independently selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl and phenyl($C_{1-4}$)alkyl;

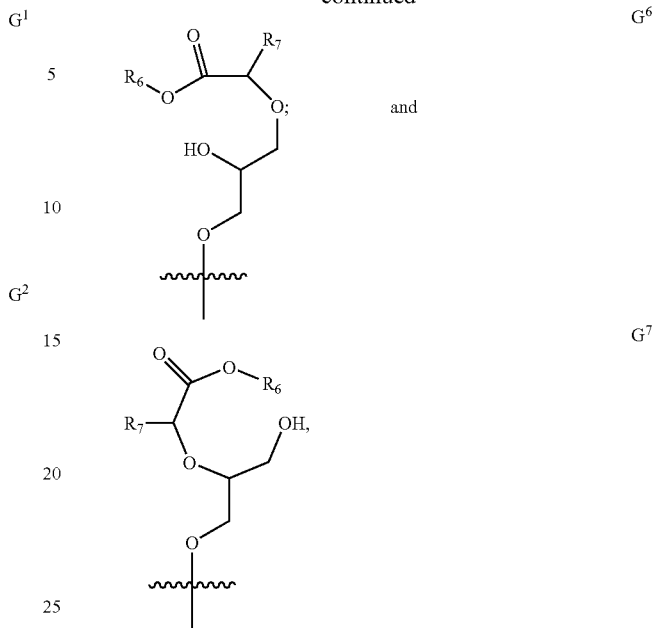

wherein $R_6$ and $R_7$ represent, in each instance, an independent substitution; preferably, $R_6$ and $R_7$ are independently selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl and phenyl($C_{1-4}$)alkyl; more preferably, $R_6$ and $R_7$ are independently selected from the group consisting of hydrogen or $C_{1-5}$ alkyl.

In the above example, the C9 double bond has been functionalized to contain an embedded dioxanone ring system across C9-10. However, the chain of the linoleic acid or derivative thereof could alternatively be functionalized with an embedded ring across C12-13. In the above example, the chain is substituted at C13 with a pendant optionally substituted or unsubstituted dioxanone ring system. However, the above example illustrates only one possible substitution pattern and the present invention is not meant to be limited to the exemplified structure. Further, in derivatives containing one or more of $G^1$-$G^7$, it is preferable that adjacent to the carbon substituted with a group of $G^1$-$G^7$ is a carbon substituted with hydroxy. A synthesis for these types of derivatives is outlined in Scheme 15 below.

Preferably, the carbons of the chain can be derivatized to contain substituents that modify the chain's physical and chemical properties in its end use application. Such modifications include those that affect surfactant properties, pour point, viscosity, crystallization, polymerization and the like. Preferably, substituents added for the above purposes include esters, alcohols, amides, amines, ketones, epoxides, carboxylic acids, alkenes, alkynes, azides, hydrazides, imines, oximes, one or more dioxanone ring systems, one or more of structures $G^3$-$G^7$ etc. More preferred substituents will be $C_{1-10}$ alkyl, $C_{1-10}$ alkoxy, $C_{6-10}$ aryl, hydroxy, heteroaryl, $C_{3-6}$ cycloalkyl, one or more optionally substituted or unsubstituted dioxanone ring systems, one or more of structures $G^3$-$G^7$, phenyl($C_{1-4}$)alkyl, aliphatic alcohols (branched or straight chain) and aliphatic amines. The addition of these substituents can lend desired chemical and physical properties to the compound, such as disruption of chain packing to prevent crystallization, or can provide chemical handles for further modification. The branched derivatives can make excellent lubricants or crystal inhibitors due to their branched nature.

The carbons of the chain can also be fully saturated with hydrogen on any carbon that is not embedded in a dioxanone ring system, wherein such an embedded carbon is bound to an oxygen.

The chain can also contain one or more sites of unsaturation within the chain.

Preferably, the carbon chain including the carbonyl carbon contains 2 to 24 carbons. More preferably, the carbon chain contains 12 to 24 carbons. Most preferably, the number of carbons is 16 to 18.

In another embodiment, the present invention is directed to a composition comprising an ester moiety attached to a carbon chain that is between 2 and 23 carbons in length, wherein the chain contains at least one dioxanone ring system, the dioxanone being formed from two adjacent carbons in the chain and having the general structure (I) shown above.

In this embodiment, the carbons of the chain can be derivatized to contain substituents that modify the chain's physical and chemical properties in its end use application. Such modifications include those that affect surfactant properties, pour point, viscosity, crystallization, polymerization and the like. Preferably, substituents added for the above purposes include esters, alcohols, amides, amines, ketones, epoxides, carboxylic acids, alkenes, alkynes, azides, hydrazides, imines, oximes, one or more dioxanone ring systems, one or more of structures $G^3$-$G^7$ etc. More preferred substituents will be $C_{1-10}$ alkyl, $C_{1-10}$ alkoxy, $C_{6-10}$ aryl, hydroxy, heteroaryl, $C_{3-6}$ cycloalkyl, one or more optionally substituted or unsubstituted dioxanone ring systems, one or more of structures $G^3$-$G^7$, phenyl($C_{1-4}$)alkyl, aliphatic alcohols (branched or straight chain) and aliphatic amines. The addition of these substituents can lend desired chemical and physical properties to the compound, such as disruption of chain packing to prevent crystallization, or can provide chemical handles for further modification. The branched derivatives can make excellent lubricants or crystal inhibitors due to their branched nature.

The carbons of the chain can also be fully saturated with hydrogen on any carbon that is not embedded in a dioxanone ring system, wherein such an embedded carbon is bound to an oxygen.

The chain may also contain one or more sites of unsaturation within the chain.

Preferably, the carbon chain including the carbonyl contains 2 to 24 carbons. More preferably, the carbon chain contains 12 to 24 carbons. Most preferably, the number of carbons is 16 to 18.

In preferred embodiments, when the composition contains an ester moiety, the chemical moiety directly attached to the ester oxygen can include any group that will form a stable ester. In more preferred embodiments, the ester is a $C_{1-4}$ alkyl ester or a polyol ester. More preferred $C_{1-4}$ alkyl esters include methyl and ethyl esters.

A polyol ester comprises an ester formed by derivatizing one of the hydroxyl groups of the polyol into an ester or polyester. Preferred polyols include glycerol, propylene glycol, ethylene glycol, diethylene glycol and dipropylene glycol. A polyol ester of the present invention comprises an ester or polyester as described above, wherein the ester is directly attached to a carbon chain that is between 2 and 23 carbons in length, wherein the chain contains at least one dioxanone ring system, the dioxanone being formed from two adjacent carbons in the chain and having the general structure (I) shown above and/or at least one carbon in the chain is substituted with a pendant dioxanone ring system or one or more of structures $G^3$-$G^7$. In another preferred embodiment, the composition is a dioxanone-containing propylene glycol monoester.

Another aspect of the present invention is directed to composition comprising a polyol polyester containing at least two ester moieties that in each instance are attached to a separate carbon chain that is between 2 and 24 carbons in length, wherein the chain contains at least one dioxanone ring system, the dioxanone being formed from two adjacent carbons in the chain and having the general structure (I) shown above and/or at least one carbon in the chain is substituted with a pendant dioxanone ring system or one or more of structures $G^3$-$G^7$.

In this embodiment, the carbons of the chain can be derivatized to contain substituents that modify the chain's physical and chemical properties in its end use application. Such modifications include those that affect surfactant properties, pour point, viscosity, crystallization, polymerization and the like. Preferably, substituents added for the above purposes include esters, alcohols, amides, amines, ketones, epoxides, carboxylic acids, alkenes, alkynes, azides, hydrazides, imines, oximes, one or more dioxanone ring systems, one or more of structures $G^3$-$G^7$ etc. More preferred substituents will be $C_{1-10}$ alkyl, $C_{1-10}$ alkoxy, $C_{6-10}$ aryl, hydroxy, heteroaryl, $C_{3-6}$ cycloalkyl, one or more optionally substituted or unsubstituted dioxanone ring systems, one or more of structures $G^3$-$G^7$, phenyl($C_{1-4}$)alkyl, aliphatic alcohols (branched or straight chain) and aliphatic amines. The addition of these substituents can lend desired chemical and physical properties to the compound, such as disruption of chain packing to prevent crystallization, or can provide chemical handles for further modification. The branched derivatives can make excellent lubricants or crystal inhibitors due to their branched nature.

The carbons of the chain can also be fully saturated with hydrogen on any carbon that is not embedded in a dioxanone ring system, wherein such an embedded carbon is bound to an oxygen.

The chain may also contain one or more sites of unsaturation within the chain.

Preferably, the carbon chain including the carbonyl carbon contains 2 to 24 carbons. More preferably, the carbon chain contains 12 to 24 carbons. Most preferably, the number of carbons is 16 to 18.

Preferably, the polyol polyester is a polyester of glycerol, propylene glycol, ethylene glycol, diethylene glycol or dipropylene glycol.

In a preferred embodiment, the polyol polyester is a polyol triester. In this embodiment, the polyol triester is a triglyceride having the following general structure (II):

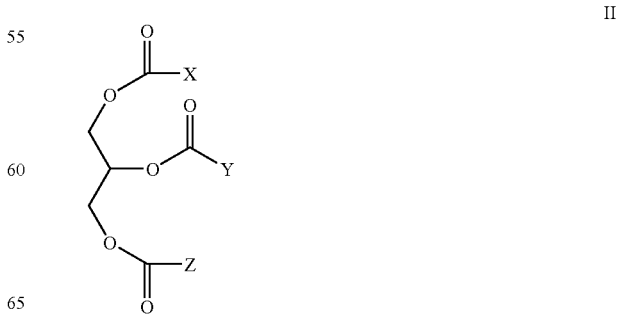

wherein X, Y and Z are independently selected from the group consisting of

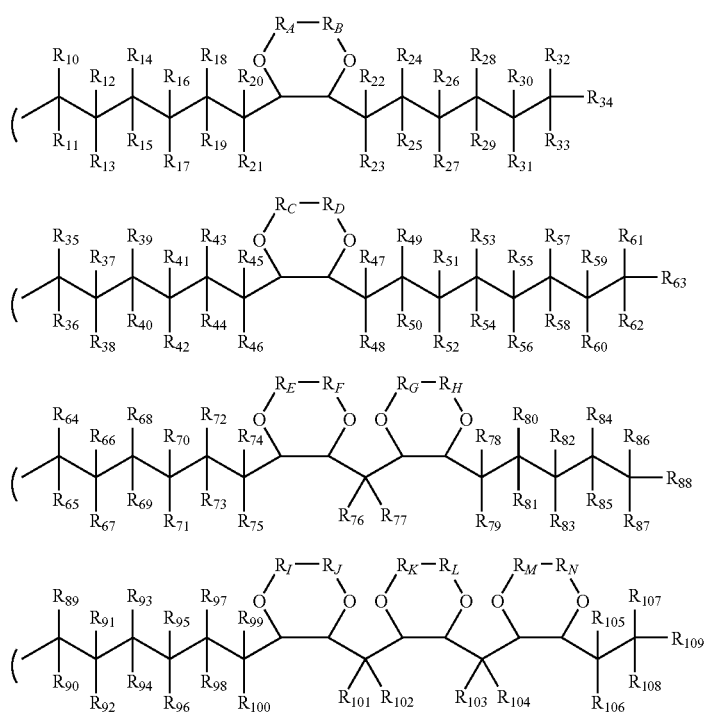

wherein, in each instance, $R_{10}$ through $R_{109}$ is independently selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl, one or more optionally substituted or unsubstituted dioxanone ring systems, one or more of structures $G^3$-$G^7$ and phenyl($C_{1-4}$)alkyl, and wherein one of each of the following groups $R_A$ and $R_B$, $R_C$ and $R_D$, $R_E$ and $R_F$, $R_G$ and $R_H$, $R_I$ and $R_J$, $R_K$ and $R_L$, $R_M$ and $R_N$, is a carbonyl, and the other of $R_A$ and $R_B$, $R_C$ and $R_D$, $R_E$ and $R_F$, $R_G$ and $R_H$, $R_I$ and $R_J$, $R_K$ and $R_L$, $R_M$ and $R_N$ is $CR_4R_5$, wherein $R_4$ and $R_5$ represent, in each instance, an independent substitution. Preferably, $R_{10}$ through $R_{109}$ represent substituents that modify the chain's physical and chemical properties in its end use application. Such modifications include those that affect surfactant properties, pour point, viscosity, crystallization, polymerization and the like. Preferably, substituents added for the above purposes include esters, alcohols, amides, amines, ketones, epoxides, carboxylic acids, alkenes, alkynes, azides, hydrazides, imines, oximes, one or more optionally substituted or unsubstituted dioxanone ring systems, one or more of structures $G^3$-$G^7$ etc. More preferred substituents will be $C_{1-10}$ alkyl, $C_{1-10}$ alkoxy, $C_{6-10}$ aryl, hydroxy, heteroaryl, $C_{3-6}$ cycloalkyl, one or more optionally substituted or unsubstituted dioxanone ring systems, one or more of structures $G^3$-$G^7$, phenyl($C_{1-4}$)alkyl, aliphatic alcohols (branched or straight chain) and aliphatic amines. The addition of these substituents can lend desired chemical and physical properties to the compound, such as disruption of chain packing to prevent crystallization, or can provide chemical handles for further modification. The branched derivatives can make excellent lubricants or crystal inhibitors due to their branched nature.

In this embodiment, the invention also describes a polyol polyester composition that contains multiple carbon chains, wherein one or more carbon chains do not contain an embedded dioxanone ring system, provided that at least one carbon chain in the composition contains at least one embedded dioxanone ring system and/or at least one carbon in the chain is substituted with a pendant dioxanone ring system or one or more of structures $G^3$-$G^7$.

The present invention is also directed to a fatty acid derivative comprising a carboxylic acid derived from a fatty acid residue from an animal oil, fish oil, a vegetable oil, a genetically-modified vegetable oil, or a chemically or enzymatically-modified vegetable oil, or mixtures or derivatives thereof, wherein the fatty acid residue contains at least one dioxanone ring system, the dioxanone being formed from two adjacent carbons in the chain and having the general structure (I) shown above and/or at least one carbon in the chain is substituted with a pendant dioxanone ring system or one or more of structures $G^3$-$G^7$.

In preferred embodiments of this aspect of the present invention, the vegetable oil is selected from the group consisting of soybean oil, linseed oil, sunflower oil, castor oil, corn oil, canola oil, rapeseed oil, palm kernel oil, cottonseed oil, peanut oil, coconut oil, palm oil, tung oil, safflower oil and derivatives and mixtures thereof. The above oils can also be conjugated.

In other preferred embodiments, the carboxylic acid is derived from palmitoleic acid, oleic acid, linoleic acid, linolenic acid, eleostearic acid, ricinoleic acid, arachidonic acid, cetoleic acid or erucic acid. The above acids can also be conjugated.

In this embodiment, the carbons of the carbon chain can be derivatized to contain substituents that modify the chain's physical and chemical properties in its end use application.

Such modifications include those that affect surfactant properties, pour point, viscosity, crystallization, polymerization and the like. Preferably, substituents added for the above purposes include esters, alcohols, amides, amines, ketones, epoxides, carboxylic acids, alkenes, alkynes, azides, hydrazides, imines, oximes, one or more dioxanone ring systems, one or more of structures $G^3$-$G^7$ etc. More preferred substituents will be $C_{1-10}$ alkyl, $C_{1-10}$ alkoxy, $C_{6-10}$ aryl, hydroxy, heteroaryl, $C_{3-6}$ cycloalkyl, one or more optionally substituted or unsubstituted dioxanone ring systems, one or more of structures $G^3$-$G^7$, phenyl($C_{1-4}$)alkyl, aliphatic alcohols (branched or straight chain) and aliphatic amines. The addition of these substituents can lend desired chemical and physical properties to the compound, such as disruption of chain packing to prevent crystallization, or can provide chemical handles for further modification. The branched derivatives can make excellent lubricants or crystal inhibitors due to their branched nature.

The carbons of the fatty acid chain can also be fully saturated with hydrogen where any carbon is not embedded in a dioxanone ring system, wherein such an embedded carbon is bound to an oxygen.

The chain can also contain one or more sites of unsaturation within the chain.

Preferably, the carbon chain including the carbonyl carbon contains 2 to 24 carbons. More preferably, the carbon chain contains 12 to 24 carbons. Most preferably, the number of carbons is 16 to 18.

The present invention is also directed to a fatty acid derivative comprising an ester moiety, wherein the carbon chain of the ester is derived from a fatty acid residue obtained from an animal oil, fish oil, a vegetable oil, a genetically-modified vegetable oil, or a chemically or enzymatically-modified vegetable oil, or mixtures or derivatives thereof and contains at least one dioxanone ring system, the dioxanone being formed from two adjacent carbons in the chain and having the general structure (I) shown above and/or at least one carbon in the chain is substituted with a pendant dioxanone ring system, or one or more of structures $G^3$-$G^7$.

In preferred embodiments, when the fatty acid derivative contains an ester moiety, the chemical moiety directly attached to the ester oxygen can include any group that will form a stable ester. In more preferred embodiments, the ester is a $C_{1-4}$ alkyl ester or a polyol ester. More preferred $C_{1-4}$ alkyl esters include methyl and ethyl esters.

In preferred embodiments of this aspect of the present invention, the vegetable oil is selected from the group consisting of soybean oil, linseed oil, sunflower oil, castor oil, corn oil, canola oil, rapeseed oil, palm kernel oil, cottonseed oil, peanut oil, coconut oil, palm oil, tung oil, safflower oil and derivatives and mixtures thereof. The above oils can also be conjugated.

In other preferred embodiments, the fatty acid residue of the ester is derived from palmitoleic acid, oleic acid, linoleic acid, linolenic acid, eleostearic acid, ricinoleic acid, arachidonic acid, cetoleic acid or erucic acid. The above acids can also be conjugated.

In this embodiment, the carbons of the chain can be derivatized to contain substituents that modify the chain's physical and chemical properties in its end use application. Such modifications include those that affect surfactant properties, pour point, viscosity, crystallization, polymerization and the like. Preferably, substituents added for the above purposes include esters, alcohols, amides, amines, ketones, epoxides, carboxylic acids, alkenes, alkynes, azides, hydrazides, imines, oximes, one or more dioxanone ring systems, one or more of structures $G^3$-$G^7$ etc. More preferred substituents will be $C_{1-10}$ alkyl, $C_{1-10}$ alkoxy, $C_{6-10}$ aryl, hydroxy, heteroaryl, $C_{3-6}$ cycloalkyl, one or more optionally substituted or unsubstituted dioxanone ring systems, one or more of structures $G^3$-$G^7$, phenyl($C_{1-4}$)alkyl, aliphatic alcohols (branched or straight chain) and aliphatic amines. The addition of these substituents can lend desired chemical and physical properties to the compound, such as disruption of chain packing to prevent crystallization, or can provide chemical handles for further modification. The branched derivatives can make excellent lubricants or crystal inhibitors due to their branched nature.

The carbons of the fatty acid chain may also be fully saturated with hydrogen where any carbon is not embedded in a dioxanone ring system, wherein such an embedded carbon is bound to an oxygen.

The chain can also contain one or more sites of unsaturation within the chain.

Preferably, the carbon chain including the carbonyl carbon contains 2 to 24 carbons. More preferably, the carbon chain contains 12 to 24 carbons. Most preferably, the number of carbons is 16 to 18.

The present invention is also directed to a fatty acid derivative comprising a polyol polyester containing at least two ester moieties that are in each instance attached to a separate fatty acid residue that is obtained from an animal oil, fish oil, a vegetable oil, a genetically-modified vegetable oil, a chemically-modified vegetable oil or an enzymatically-modified vegetable oil, copolymer oil, or mixtures or derivatives thereof, and contains at least one dioxanone ring system, the dioxanone being formed from two adjacent carbons in the chain and having the general structure (I) shown above and/or at least one carbon in the chain is substituted with a pendant dioxanone ring system, or one or more of structures $G^3$-$G^7$.

A polyol ester comprises an ester formed by derivatizing one of the hydroxyl groups of the polyol into an ester. Preferred polyols include glycerol, propylene glycol, ethylene glycol, diethylene glycol and dipropylene glycol. A polyol ester of the present invention comprises an ester or polyester as described above, wherein the ester is directly attached to a carbon chain that is between 2 and 24 carbons in length wherein, the chain contains at least one dioxanone ring system, the dioxanone being formed from two adjacent carbons in the chain and having the general structure (I) shown above and/or at least one carbon in the chain is substituted with a pendant dioxanone ring system or one or more of structures $G^3$-$G^7$. In another preferred embodiment, the ester is a dioxanone-containing propylene glycol monoester.

In preferred embodiments of this aspect of the present invention, the vegetable oil is selected from the group consisting of soybean oil, linseed oil, sunflower oil, castor oil, corn oil, canola oil, rapeseed oil, palm kernel oil, cottonseed oil, peanut oil, coconut oil, palm oil, tung oil, safflower oil and derivatives and mixtures thereof. The above oils can also be conjugated.

In other preferred embodiments, the carboxylic acid is derived from palmitoleic acid, oleic acid, linoleic acid, linolenic acid, eleostearic acid, ricinoleic acid, arachidonic acid, cetoleic acid or erucic acid. The above acids can also be conjugated.

In this embodiment, the carbons of the chain can be derivatized to contain substituents that modify the chain's physical and chemical properties in its end use application. Such modifications include those that affect surfactant properties, pour point, viscosity, crystallization, polymerization and the like. Preferably, substituents added for the above purposes include esters, alcohols, amides, amines, ketones, epoxides, carboxylic acids, alkenes, alkynes, azides, hydrazides, imines, oximes, one or more dioxanone ring systems, one or more of structures $G^3$-$G^7$ etc. More preferred substituents will be $C_{1-10}$ alkyl, $C_{1-10}$ alkoxy, $C_{6-10}$ aryl, hydroxy, heteroaryl, $C_{3-6}$ cycloalkyl, one or more optionally substituted or unsubstituted dioxanone ring systems, one or more of structures $G^3$-$G^7$, phenyl($C_{1-4}$)alkyl, aliphatic alcohols (branched or straight chain) and aliphatic amines. The addition of these substituents can lend desired chemical and physical properties to the compound, such as disruption of chain packing to prevent crystallization, or can provide chemical handles for further modification. The branched derivatives can make excellent lubricants or crystal inhibitors due to their branched nature.

The carbons of the chain may also be fully saturated with hydrogen on any carbon that is not embedded in a dioxanone ring system, wherein such an embedded carbon is bound to an oxygen.

The chain can also contain one or more sites of unsaturation within the chain.

Preferably, the carbon chain including the carbonyl carbon contains 2 to 24 carbons. More preferably, the carbon chain contains 12 to 24 carbons. Most preferably, the number of carbons is 16 to 18.

Preferably, the polyol polyester is a polyester of glycerol, propylene glycol, ethylene glycol, diethylene glycol or dipropylene glycol.

In a preferred embodiment, the polyol polyester is a polyol triester. In this embodiment, the polyol triester is a triglyceride.

In one embodiment, the present invention utilizes the triglycerides obtained directly from one or more of the oils listed above.

In another aspect, the present invention is directed to a fatty acid derivative comprising a carboxyl or ester moiety that is attached to a carbon chain which contains at least one dioxanone ring system (embedded or pendant) formed by combining an alpha hydroxy ester with an epoxidized fatty acid carbon chain.

In this embodiment, the alpha hydroxy ester has the following general structure (III):

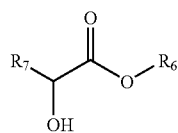

III wherein $R_6$ and $R_7$ represent, in each instance, an independent substitution. Preferably, $R_6$ and $R_7$ are independently selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl and phenyl($C_{1-4}$)alkyl. More preferably, $R_6$ and $R_7$ are independently selected from the group consisting of hydrogen or $C_{1-5}$ alkyl.

Although not limiting the scope of the invention to this theory, the reaction described above and illustrated in Schemes 1, 2, 5 and 7 below proceeds via nucleophilic attack of the alcohol on an oxirane carbon followed by attack of the resulting hydroxyl on the carbony to complete transesterification. Thus, the present invention also contemplates the use of an alpha hydroxy acid chloride or other leaving group in place of the O—$R_6$ group.

In another aspect, the present invention is directed to a fatty acid derivative comprising a polyol polyester that contains at least one fatty acid residue, wherein the residue in each instance contains at least one dioxanone ring system (embedded or pendant), the dioxanone being formed by combining an epoxidized animal oil, fish oil, vegetable oil, genetically-modified vegetable oil, chemically-modified vegetable oil or enzymatically-modified vegetable oil, copolymer oil or polymerized oil or mixtures or derivatives thereof and a alpha hydroxy ester.

In this embodiment, the epoxidized vegetable oil, genetically-modified vegetable oil, chemically-modified vegetable oil or enzymatically-modified vegetable oil, copolymer oil fatty acid ester carbon chain can be partially epoxidized. Partial epoxation forms an epoxidized oil that retains some of the original bouble bonds.

In another aspect, the present invention is directed to a fatty acid derivative having the following general structure (IV):

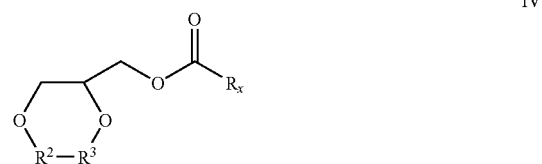

IV wherein one of $R^2$ and $R^3$ is a carbonyl and the other of $R^2$ and $R^3$ is $CR_4R_5$, and wherein $R_4$ and $R_5$ are independently selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl and phenyl($C_{1-4}$)alkyl, and $R_x$ is a carbon chain that is 2 to 23 carbons in length.

In this embodiment, the carbons of the chain can be derivatized to contain substituents that modify the chain's physical and chemical properties in its end use application. Such modifications include those that affect surfactant properties, pour point, viscosity, crystallization, polymerization and the like. Preferably, substituents added for the above purposes include esters, alcohols, amides, amines, ketones, epoxides, carboxylic acids, alkenes, alkynes, azides, hydrazides, imines, oximes, one or more dioxanone ring systems, one or more of structures $G^3$-$G^7$ etc. More preferred substituents will be $C_{1-10}$ alkyl, $C_{1-10}$ alkoxy, $C_{6-10}$ aryl, hydroxy, heteroaryl, $C_{3-6}$ cycloalkyl, one or more optionally substituted or unsubstituted dioxanone ring systems, one or more of structures $G^3$-$G^7$, phenyl($C_{1-4}$)alkyl, aliphatic alcohols (branched or straight chain) and aliphatic amines. The addition of these substituents can lend desired chemical and physical properties to the compound, such as disruption of chain packing to prevent crystallization, or can provide chemical handles for further modification. The branched derivatives can make excellent lubricants or crystal inhibitors due to their branched nature.

The carbons of the chain can also be fully saturated with hydrogen on any carbon that is not embedded in a dioxanone ring system, wherein such an embedded carbon is bound to an oxygen.

The chain can also contain one or more sites of unsaturation within the chain.

Preferably, the carbon chain including the carbonyl carbon contains 2 to 24 carbons. More preferably, the carbon chain contains 12 to 24 carbons. Most preferably, the number of carbons is 16 to 18.

In this embodiment, it is also preferred that the carbon chain is a fatty acid residue derived from the group consisting of palmitoleic acid, oleic acid, linoleic acid, linolenic acid, eleostearic acid, ricinoleic acid, arachidonic acid, cetoleic acid and erucic acid.

The present invention is also directed to fatty acid derivatives and compositions comprising the following general structure:

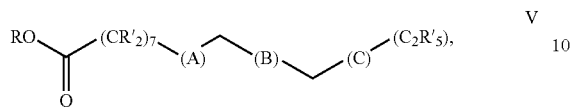
V wherein R is hydrogen or $C_{1-4}$ alkyl; (A), (B) and (C) are each independently selected from the group consisting of:

v.

wherein R' is selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl, one or more optionally substituted or unsubstituted dioxanone ring systems and phenyl($C_{1-4}$)alkyl;

vi.

wherein R' is as described above;

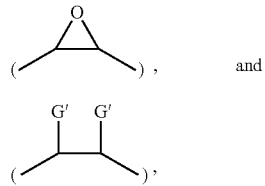
vii.

and viii.

wherein G', in each instance, is independently selected from the group consisting of hydrogen, hydroxy, $G^1$, $G^2$, $G^3$, $G^4$, $G^5$, $G^6$ and $G^7$, wherein $G^1$, $G^2$, $G^3$, $G^4$, $G^5$, $G^6$ and $G^7$ have the following structures:

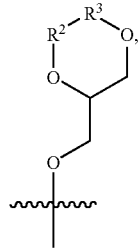
$G^1$

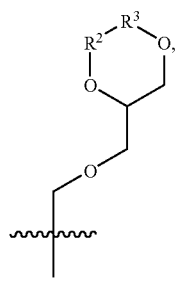
$G^2$ wherein one of $R^2$ and $R^3$ is a carbonyl and the other of $R^2$ and $R^3$ is $CR_4R_5$, and wherein $R_4$ and $R_5$ are independently selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl and phenyl(C1-4)alkyl;

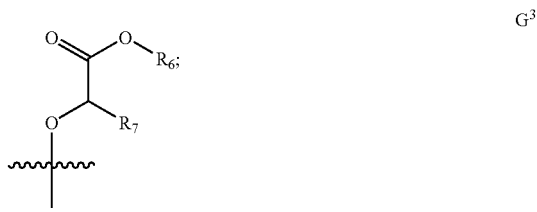
$G^3$

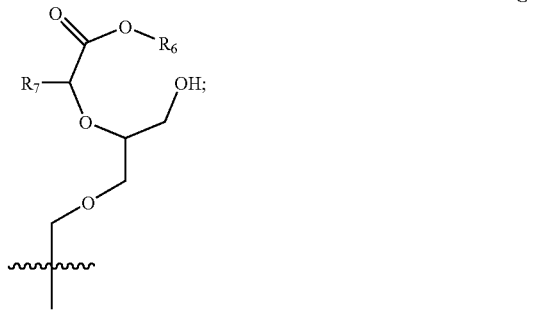
$G^4$

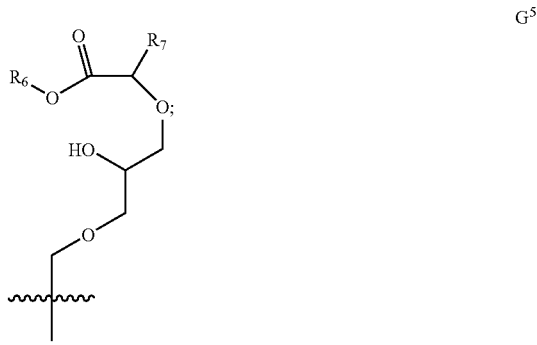
$G^5$

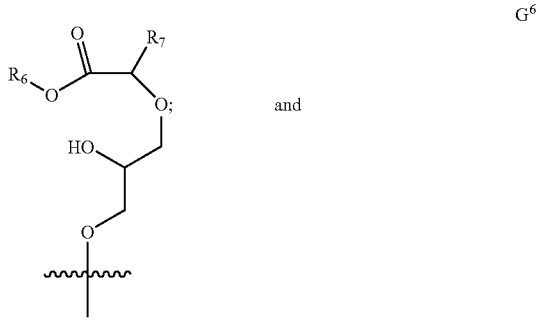
$G^6$ and

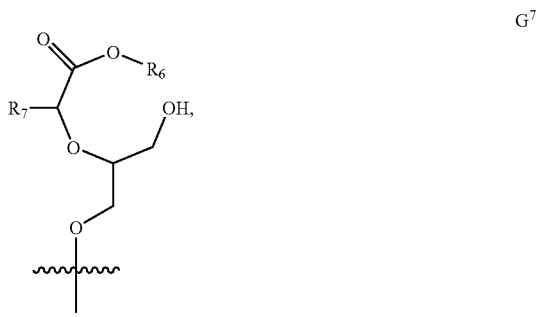
$G^7$ wherein R₆ and R₇ represent, in each instance, an independent substitution; preferably, R₆ and R₇ are independently selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl and phenyl($C_{1-4}$)alkyl; more preferably, R₆ and R₇ are independently selected from the group consisting of hydrogen or $C_{1-5}$ alkyl;

provided that at least one of (A), (B) or (C) is

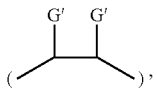
viii.

wherein, at least one G' is G¹, G², G³, G⁴, G⁵, G⁶ or G⁷.

Especially useful compositions comprise the above structure V where (B) and (C) are each —(CR'₂CR'₂)—. These types of structures can be derived for instance from oleic acid. Preferably, each R' is selected from the group consisting of hydrogen, $C_{1-10}$ alkyl $C_{1-10}$ alkoxy, $C_{6-10}$ aryl, hydroxy, heteroaryl, $C_{3-6}$ cycloalkyl, one or more optionally substituted or unsubstituted dioxanone ring systems, one or more of structures G³-G⁷ and phenyl($C_{1-4}$)alkyl. More preferably, R' in each instance is hydrogen. In this embodiment, useful compounds include those where G' is, in each case, independently selected from the group consisting of hydrogen, hydroxy, G¹, G², G³, G⁴, G⁵, G⁶ and G⁷, wherein G¹, G², G³, G⁴, G⁵, G⁶ and G⁷ are as shown above. More preferably, G' is G¹, G², G³, G⁴, G⁵, G⁶ or G⁷.

Especially useful compositions also include the above structure V where (C) is —(CR'₂CR'₂)—. These types of structures can be derived for instance from linoleic acid. Preferably, each R' is selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl, one or more optionally substituted or unsubstituted dioxanone ring systems, one or more of structures G³-G⁷ and phenyl($C_{1-4}$)alkyl. More preferably, R' in each instance is hydrogen. In this embodiment, useful compounds include those where G' is, in each case, independently selected from the group consisting of hydrogen, hydroxy, G¹, G², G³, G⁴, G⁵, G⁶ and G7. More preferably, one of G' is G¹, G², G³, G⁴, G⁵, G⁶ and G⁷, the other is hydrogen or hydroxy.

Especially useful compositions also include the above structure V where one of (A), (B) and (C) is selected from the group consisting of:

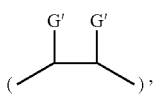
viii.

wherein one of G' is $C_{1-4}$ alkyl or hydroxy;
and

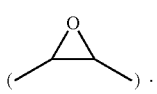
vii.

In all embodiments of structure V, there is at least one of (A), (B) or (C) that is

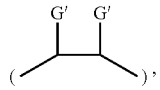

i.e. Structure viii, wherein one of G' is G¹, G², G³, G⁴, G⁵, G⁶ or G⁷. It is most preferable that the other of G' is hydrogen or hydroxy.

The present invention is also directed to a coating composition comprising a latex resin and a composition described herein comprising a carbon chain 2 to 24 carbons in length, wherein in at least one instance two adjacent carbons of the chain are embedded in a dioxanone ring system, and/or the carbon chain is substituted with a pendant dioxanone ring system or one or more of structures G³-G⁷ as described herein. Also preferred is a coating composition comprising a latex resin and a dioxanone-containing fatty acid derivative (acid, ester, polyester, etc.) as described herein. Preferably, the coating composition also contains a monoamine component such as diethylamine. The monoamine can react with the dioxanone and form a urethane. The coating composition can further comprise additives, surfactants, pigments, modifiers and the like.

The present invention is also directed to a polymer composition comprising: 1.) a composition described herein comprising a carbon chain 2 to 24 carbons in length, wherein in at least one instance two adjacent carbons of said chain are embedded in a dioxanone ring system, and/or the carbon chain is substituted with a pendant dioxanone ring system or one or more of structures G³-G⁷ as described herein, and 2.) a diamine component. Also preferred is a polymer composition comprising a fatty acid derivative as described herein and a diamine component. When the composition or the fatty acid derivative is combined with a diamine, the diamine can crosslink the carbon chains by forming a urethane linkage on separate chains at each amine of the diamine, thereby forming a polymer.

The present invention is also directed to a polymer composition comprising: 1.) a composition described herein comprising a carbon chain 2 to 24 carbons in length, wherein in at least one instance two adjacent carbons of said chain are embedded in a dioxanone ring system, and/or the carbon chain is substituted with a pendant dioxanone ring system or one or more of structures G³-G⁷ as described herein, and 2.) a polyethylene glycol (PEG) polymer. Also preferred is a polymer composition comprising, a fatty acid derivative as described herein and a polyethylene glycol (PEG) component. See Scheme 8 and Example 4.

The present invention is also directed to a method of preparing a coating composition comprising combining a latex resin, a dioxanone containing composition or fatty acid derivative (acid, ester, polyester, etc.) described herein, and a monoamine, wherein a coating composition is prepared.

The present invention is also directed to a method of preparing a polymer composition comprising combining a dioxanone containing composition or fatty acid derivative (acid, ester, polyester, etc.) described herein with a diamine, wherein a polymer is prepared.

The present invention is also directed to a method of preparing a polymer composition comprising combining a dioxanone containing composition or fatty acid derivative described herein with a PEG polymer, wherein a polymer is prepared.

The present invention is also directed to compositions comprising a fatty acid derivative as described herein containing one or more double bonds that have been converted to a hydroxy substitutent as shown in Scheme 13. The hydroxy-substituted fatty acid chain can further contain one or more double bonds that have not been converted. Vegetable oils bearing hydroxyl groups are important ingredients for coatings, surfactants and plastics. These derivatives are especially suited for use in compositions that utilize castor oil. Natural oils like castor contain high levels of ricinoleic acid. This C18 acid contains a C=C bond in the 9,10 position and a —OH group at position 12. Unfortunately, castor bean also contains ricin toxin that poses risks to operators during processing. In addition, it is produced in lower volumes than oils such as soybean. Hydroxylated fatty acid esters of soybean oil would essentially have similar functionality to castor, but allow for expanded supply, increased functionality and lower risk to human health. A method to hydroxylate oils is to first epoxidize or partially epoxidize the oil or fatty acid derivative and then ring open the oxirane. This gives vicinal diol functionality. Epoxide groups can also be hydrogenated to produce one —OH group from the oxirane ring. Partially epoxidized oils can be selectively hydrogenated to produce one —OH group from each oxirane without hydrogenating C=C double bonds. The hydroxylated fatty acid derivatives containing both C=C double bonds and —OH groups would have similar functionality to castor oil. In this embodiment, the hydroxy substituted fatty acid derivatives can replace the use of naturally derived castor oil in a wide variety of products. In another embodiment, the present invention is directed to a method of preparing hydroxy substituted fatty acid derivatives as outlined in Scheme 13. The advantage of this process is that it produces a fatty acid derivative that has similar properties of castor oil, but without the notorious problems associated with processing of toxic natural castor oil. In this embodiment, the invention is also directed to product compositions comprising hydroxy substituted fatty acid derivatives derived from fatty acids found in oils other than castor oil, where such derivatives have similar properties of castor oil, and thus replace or reduce the amount of castor oil used in the product.

The term "alkyl" as employed herein by itself or as part of another group refers to both straight and branched chain radicals of up to 10 carbons, preferably 6 carbons, more preferably 4 carbons, such as methyl, ethyl, propyl, isopropyl, butyl, t-butyl, and isobutyl.

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1-4 carbon atoms in length.

The term "aryl" as used herein by itself or as part of another group refers to monocyclic or bicyclic aromatic groups containing from 6 to 12 carbons in the ring portion, preferably 6-10 carbons in the ring portion, such as the carbocyclic groups phenyl, naphthyl or tetrahydronaphthyl. The term "aryl" can represent carbocyclic aryl groups, such as phenyl, naphthyl or tetrahydronaphthyl, as well as heterocyclic aryl ("heteroaryl") groups, such as pyridyl, pyrimidinyl, pyridazinyl, furyl, and pyranyl.

The term "heteroaryl" as used herein refers to groups having 5 to 14 ring atoms; 6, 10 or 14 π-electrons shared in a cyclic array; and containing carbon atoms and 1, 2 or 3 oxygen, nitrogen or sulfur heteroatoms. Examples of heteroaryl groups include thienyl, imadizolyl, oxadiazolyl, isoxazolyl, triazolyl, pyridyl, pyrimidinyl, pyridazinyl, furyl, pyranyl, thianthrenyl, pyrazolyl, pyrazinyl, indolizinyl, isoindolyl, isobenzofuranyl, benzoxazolyl, xanthenyl, 2H-pyrrolyl, pyrrolyl, 3H-indolyl, indolyl, indazolyl, purinyl, 4H-quinolizinyl, isoquinolyl, quinolyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, and phenoxazinyl groups. Especially preferred heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

The term "cycloalkyl" as used herein by itself or as part of another group refers to cycloalkyl groups containing 3 to 9 carbon atoms, more preferably, 3 to 8 carbon atoms. Typical examples are cyclopropyl, cyclobutyl, cyclopentyl, cyclohexyl, cycloheptyl, cyclooctyl and cyclononyl.

The term "phenyl($C_{1-4}$)alkyl" as used herein refers to $C_{1-4}$ alkyl groups as referred to above having an phenyl substituent and includes benzyl.

When any variable occurs more than one time in any constituent its definition on each occurrence is independent of its definition at every other occurrence. Also, combinations of substituents and/or variables are permissible only if such combinations result in stable compounds.

It is understood that the present invention encompasses the use of stereoisomers, diastereomers and optical isomers.

Schemes 1-15 exemplify a method of synthesizing dioxanone containing compositions and fatty acid derivatives as described herein as well as the synthesis of amides and polymers from said compositions and derivatives.

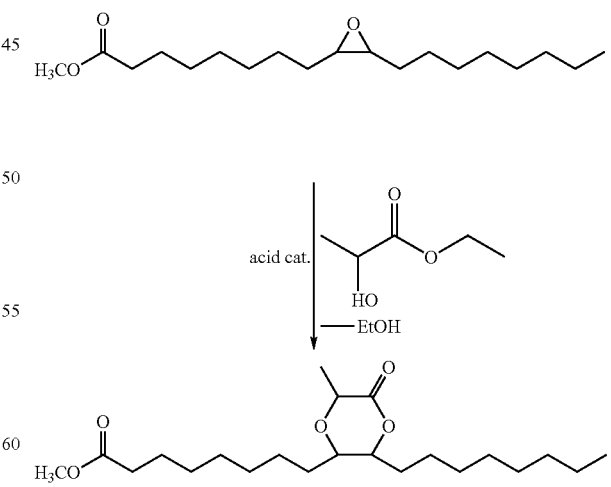

Scheme 1 depicts the synthesis of a methyl ester containing a carbon chain that has been derivatized wherein two adjacent carbons in the carbon chain are embedded in a dioxanone ring system.

SCHEME 2
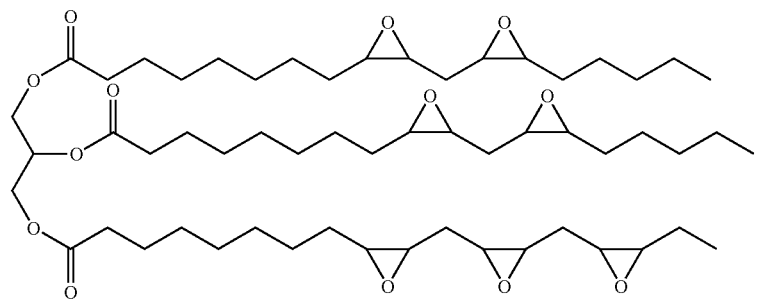
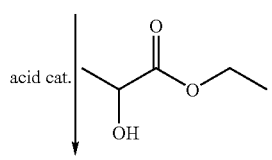
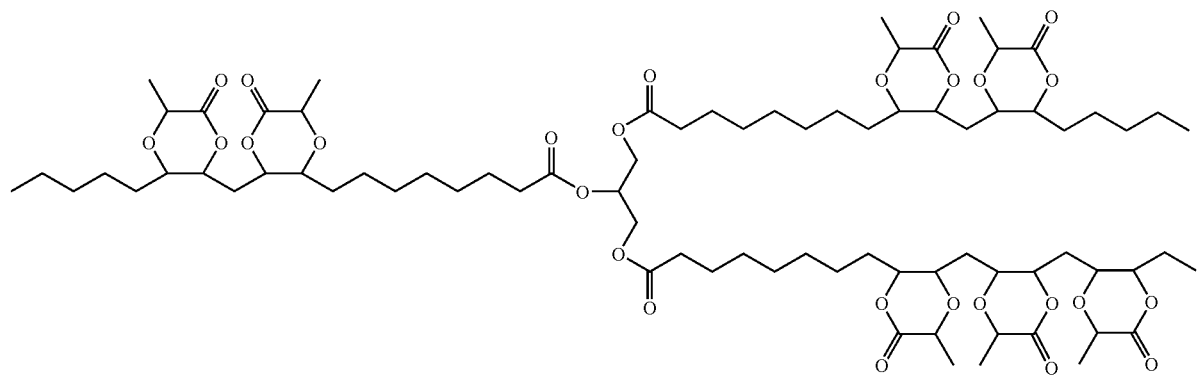
Scheme 2 depicts the synthesis of a polyol polyester that is a triglyceride, wherein each carbon chain contains an embedded dioxanone ring system.
SCHEME 3
Scheme 3 depicts the synthesis of an amide by combining a composition described herein or a fatty acid derivative described herein with a monoamine.

SCHEME 4
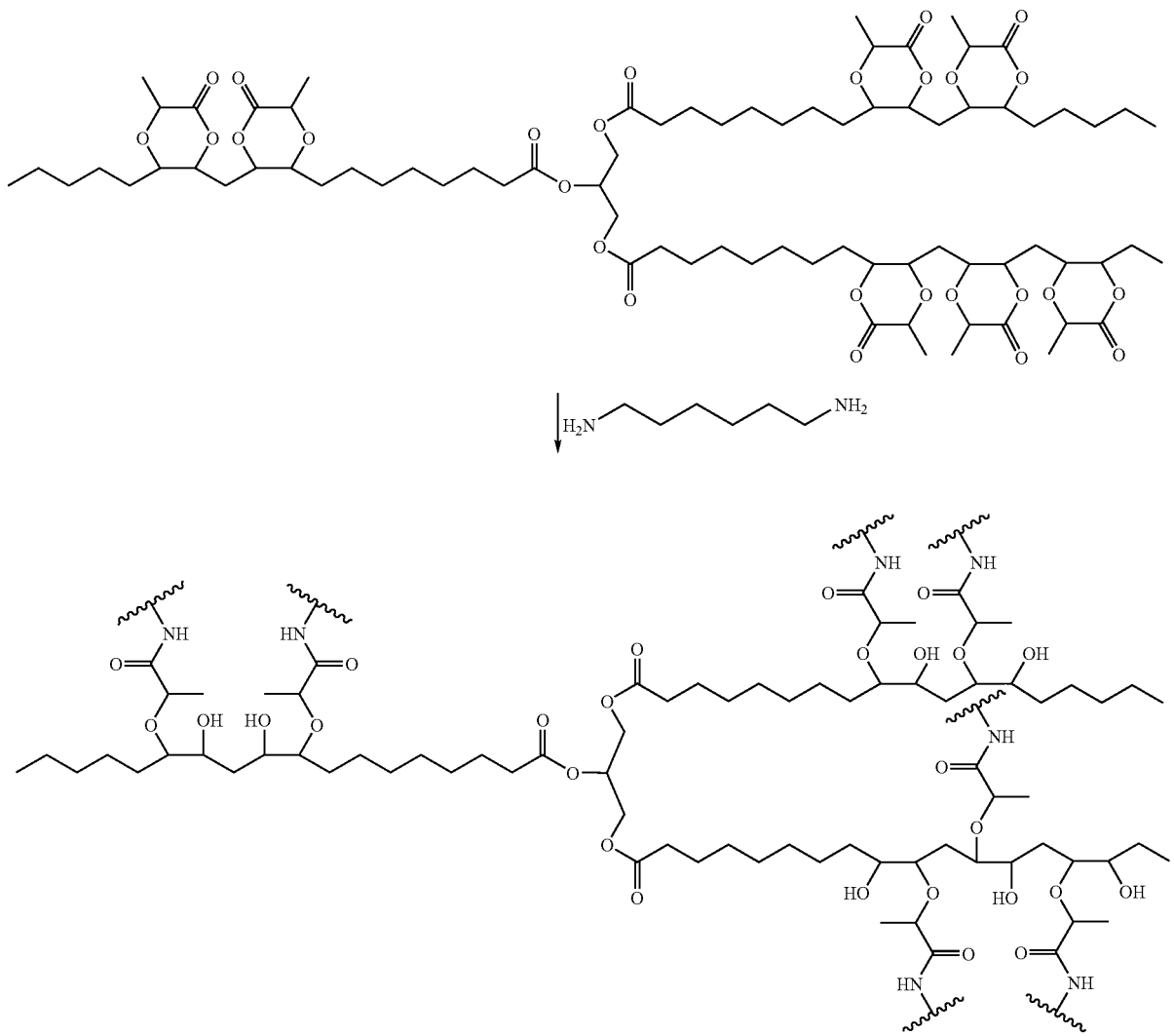
Scheme 4 depicts the synthesis of a crosslinking polymer by combining a composition described herein or a fatty acid derivative described herein with a diamine.
SCHEME 5
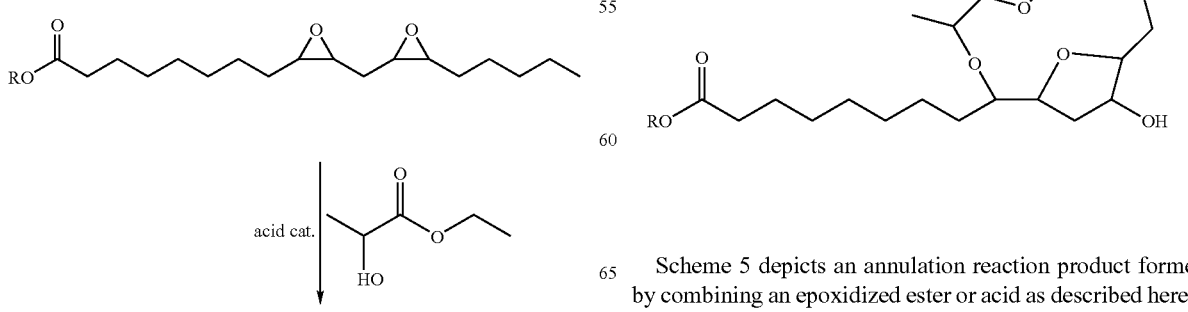
Scheme 5 depicts an annulation reaction product formed by combining an epoxidized ester or acid as described herein with a hydroxy acid ester.

SCHEME 6
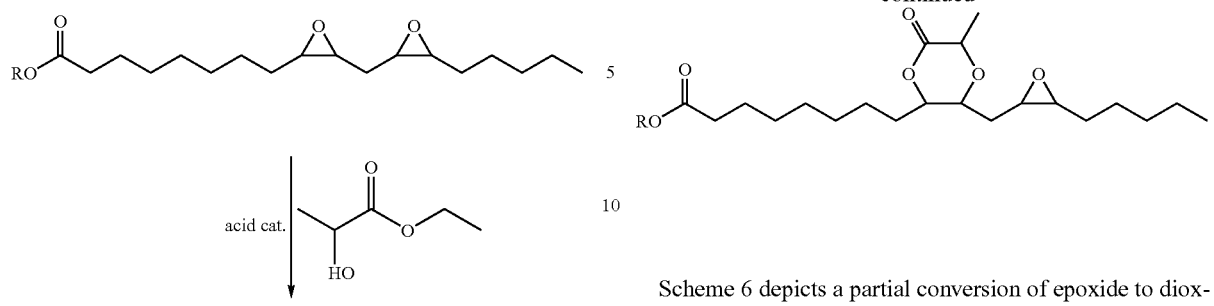
Scheme 6 depicts a partial conversion of epoxide to dioxanone.
SCHEME 7
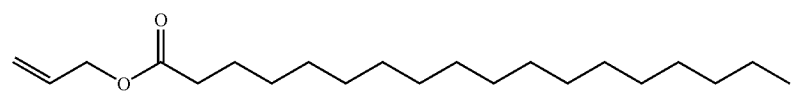
epoxidation
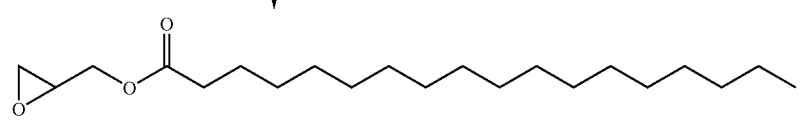
acid cat.
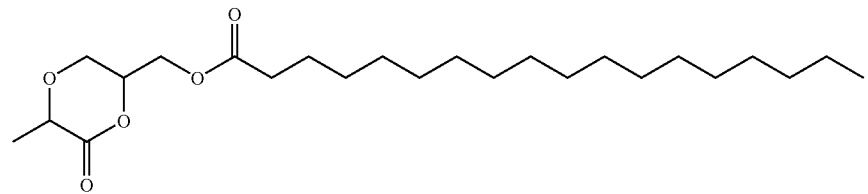
Scheme 7 depicts a terminal dioxanone composition or fatty acid derivative as described herein.
SCHEME 8
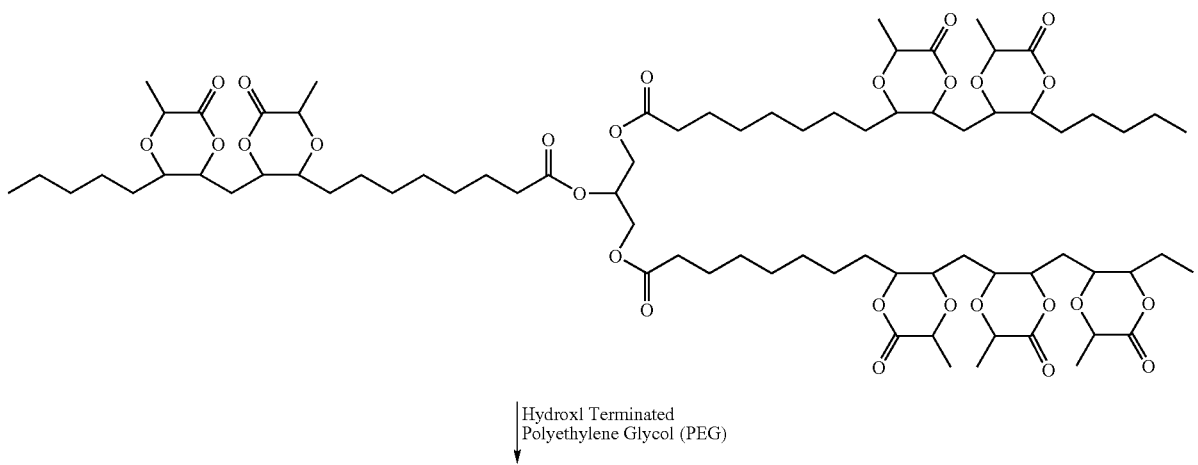
Hydroxl Terminated Polyethylene Glycol (PEG)

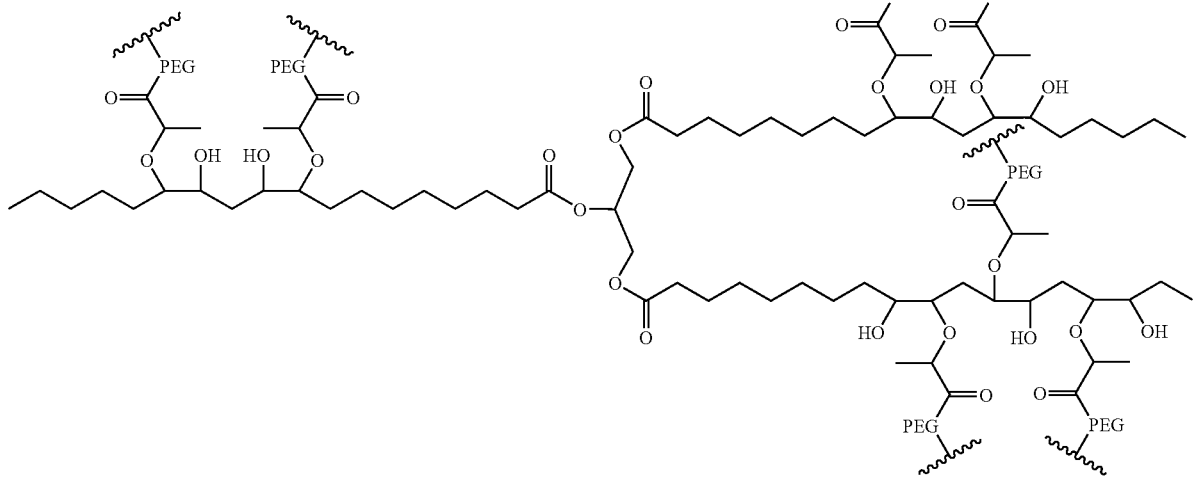

Scheme 8 depicts the formation of a thermoset polymer by combining a dioxanone-containing composition or fatty acid derivative described herein with a PEG polymer.

SCHEME 9

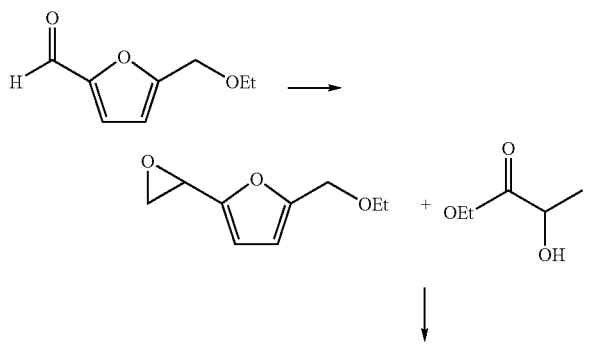

-continued

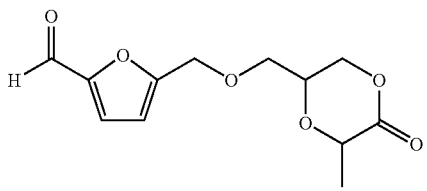

Scheme 10

Schemes 9 and 10 depict dioxanone functionalization of HMF, such as 2,5-hydroxymethyl furfural, or isosorbide derivatives.

Scheme 11 depicts formation of an embedded dioxanone ring system formed from an HMF derivative (such as the ethyl ester depicted above derived from 2,5-hydroxyethylfurfural) derivative and CR═CR', where CR═CR' represent a double bond in a carbon chain derived from a fatty acid.

SCHEME 12

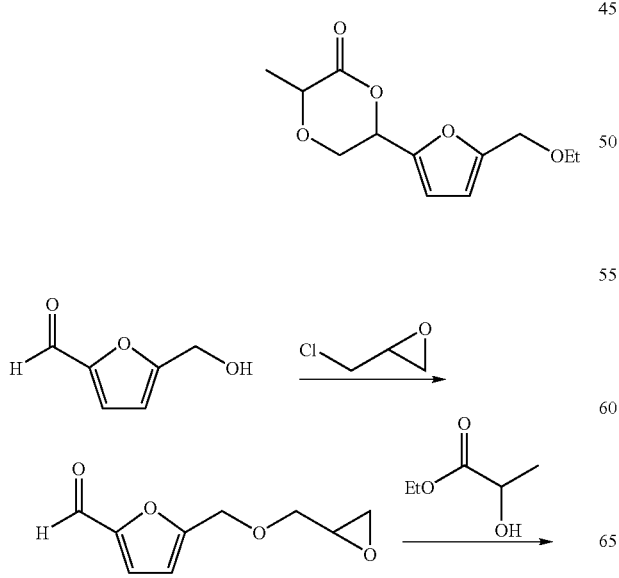

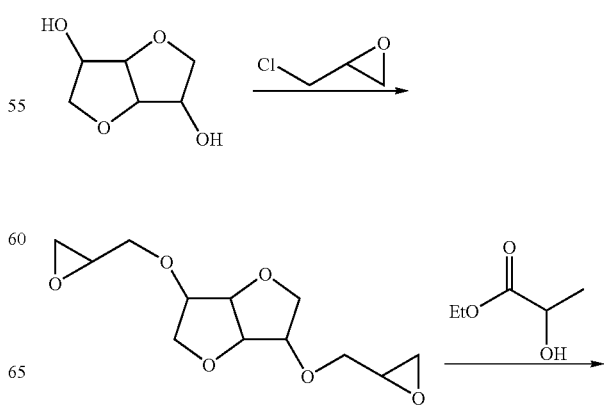

27

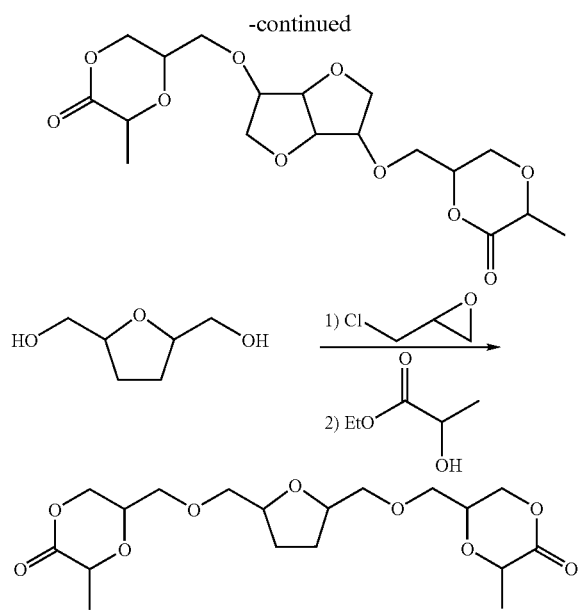

Scheme 12 depicts diepoxide derivatives of isosorbide and 2,5(bishydroxxy)tetrahydrofuran, each of which has been functionalized with more than one dioxanone ring system.

SCHEME 13

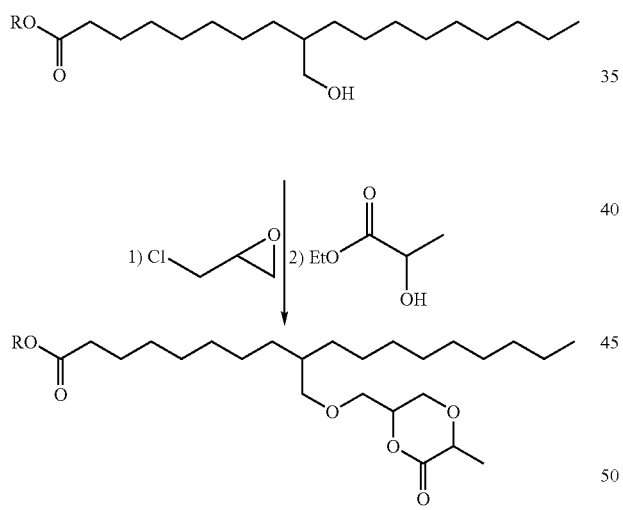

SCHEME 14

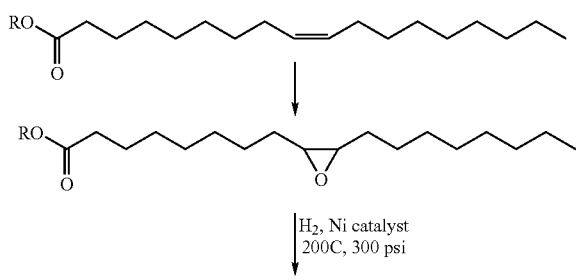

28

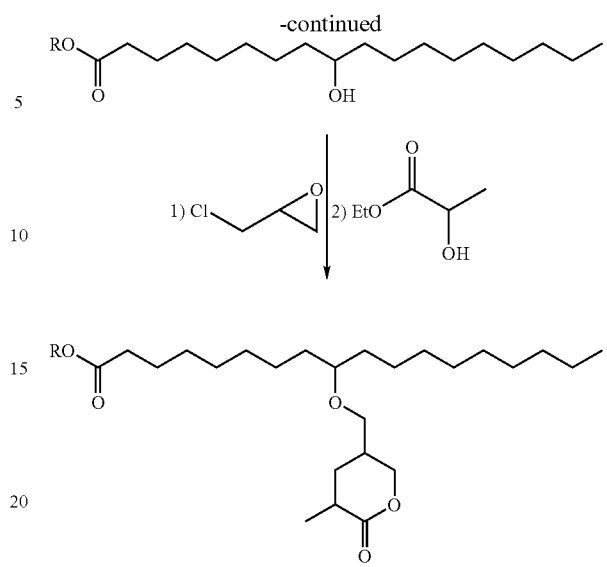

Schemes 13 and 14 depict functionalization of a pendant dioxanone ring system onto the chain of hydroxymethyl stearic acid. The nickel catalyzed reduction can be replaced by reduction using $NaBH_4$.

SCHEME 15

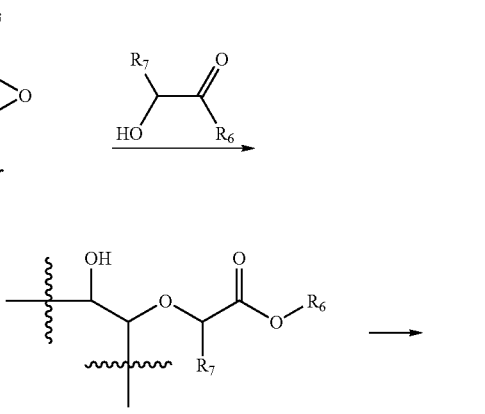

Scheme 15 depicts a synthetic route to the pendant substituent structure $G^3$ as described herein. This route also yields a hydroxy substituted carbon adjacent to the $G^3$ substituted carbon. Synthesis of $G^4$-$G^7$ can be accomplished via the same route. These structures are stable and can be contained in the compounds and compositions disclosed herein. As shown above, the structure can undergo annulation to yield an embedded dioxanone ring system. Other G structures can undergo similar annulation to yield pendant dioxanone ring systems.

EXAMPLES

Example 1

Crystallization

Substitution of fatty acid ester dioxanone can be accomplished with a nucleophile such as diethylamine. See Scheme 3. Branching off the side of fatty acid derivatives will help reduce the onset of crystallization.

Example 2

Cross-Linked Networks

Triglycerides bearing dioxanone functionality can be combined with multifunctional nucleophiles such as hexamethylenediamine to produce cross-linked networks. See Scheme 4.

Example 3

Intrachain Cyclic Structures

Internal attack of the free hydroxyl on a vicinal epoxide can form cyclic structures. See Scheme 5.

Example 4

Thermoset Polymer

A dioxanone functionalized triglyceride could be reacted with a hydroxyl terminated polyethylene glycol (PEG) to from a thermoset polymer. See Scheme 8. The size of the PEG and the crosslink density could be controlled to produce membranes that vary in hydrophobicity and pore size. The membranes could be used in various separation techniques.

Having now fully described this invention, it will be understood to those of ordinary skill in the art that the same can be performed within a wide and equivalent range of conditions, formulations, and other parameters without affecting the scope of the invention or any embodiment thereof.

All documents, e.g., scientific publications, patents, patent applications and patent publications, recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

What is claimed is:

1. A composition comprising a moiety selected from the group consisting of
   a carboxyl moiety attached to a carbon chain that is 8 to 23 carbons in length, wherein the chain contains at least one dioxanone ring system and one or more sites of unsaturation;
   an ester moiety attached to a carbon chain that is 8 to 23 carbons in length, wherein the chain contains at least one dioxanone ring system and one or more sites of unsaturation; and,
   a polyester containing at least two ester moieties each of which is attached to a separate carbon chain that is 8 to 23 carbons in length, wherein at least one of said chains contains at least one dioxanone ring system and one or more sites of unsaturation;
   said dioxanone being formed from two adjacent carbons in the chain and having the following general structure (I):

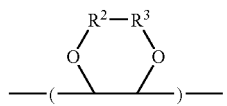

wherein one of $R^2$ and $R^3$ is a carbonyl and the other of $R^2$ and $R^3$ is $CR_4R_5$, and,
  wherein $R_4$ and $R_5$ are independently selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl, phenyl($C_{1-4}$)alkyl and

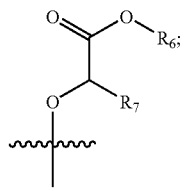

wherein $R_6$ is hydrogen or $C_{1-4}$ alkyl; and $R_7$ is selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl and phenyl($C_{1-4}$) alkyl.

2. The composition of claim 1, wherein said unsaturated carbon chain contains 16 to 18 carbons.

3. The composition of claim 1, wherein said ester is an ester of glycerol, propylene glycol, ethylene glycol, diethylene glycol or dipropylene glycol.

4. The composition of claim 3, wherein said ester is a propylene glycol monoester.

5. The composition of claim 1, wherein the moieties comprise a fatty acid residue containing at least one dioxanone ring system, wherein said residue is obtained from an animal oil, fish oil, a vegetable oil, a genetically-modified vegetable oil, a chemically-modified vegetable oil or enzymatically-modified vegetable oil, copolymer oil, or mixtures or derivatives thereof.

6. A coating composition comprising a latex resin and the fatty acid residue of claim 5.

7. A polymer composition comprising the fatty acid residue of claim 5 and a diamine, wherein said polymer is formed by combining said fatty acid derivative and said diamine.

8. A polymer composition comprising the fatty acid residue of claim 5, wherein at least one said dioxa none ring system has been combined with a polyethylene glycol to form said polymer composition.

9. A method of preparing a coating composition comprising, combining a latex resin, a fatty acid residue of claim 5 and a monoamine, wherein a coating composition is prepared.

10. A method of preparing a polymer composition comprising combining a fatty acid residue of claim 5 with a diamine, wherein a polymer is prepared.

11. A composition comprising a moiety selected from the group consisting of a carboxyl moiety attached to a carbon chain that is 2 to 23 carbons in length, wherein the chain contains at least one dioxanone ring system and one or more sites of unsaturation; an ester moiety attached to a carbon chain that is 2 to 23 carbons in length, wherein the chain contains at least one dioxanone ring system and one or more sites of unsaturation; and, a polyester containing at least two ester moieties each of which is attached to a separate carbon chain that is 2 to 23 carbons in length, wherein at least one of said chains contains at least one dioxanone ring system and one or more sites of unsaturation; said dioxanone being formed from two adjacent carbons in the chain and having the following general structure (I):

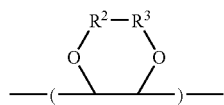
I wherein one of $R^2$ and $R^3$ is a carbonyl and the other of $R^2$ and $R^3$ is $CR_4R_5$, and wherein $R_4$ and $R_5$ are independently selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl and phenyl($C_{1-4}$)alkyl, wherein said carbons of said carbon chain are independently substituted with one or more substituents selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl, one or more optionally substituted or unsubstituted dioxanone ring systems, phenyl($C_{1-4}$)alkyl, aliphatic alcohols (branched or straight chain), aliphatic amines,

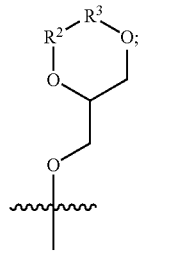
$G^1$

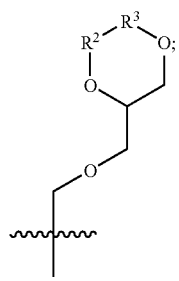
$G^2$ wherein one of $R^2$ and $R^3$ is a carbonyl and the other of $R^2$ and $R^3$ is $CR_4R_5$, and wherein $R_4$ and $R_5$ are independently selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl and phenyl($C_{1-4}$)alkyl;

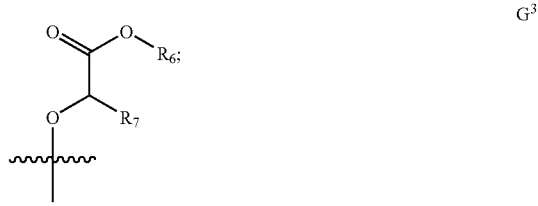
$G^3$

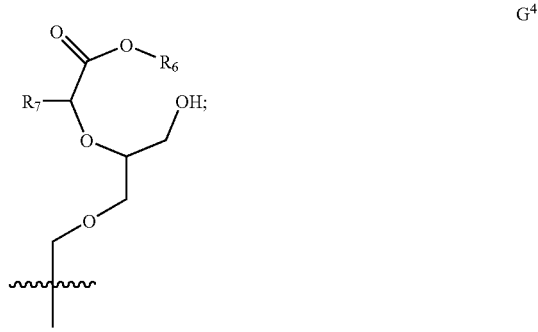
$G^4$ $G^5$

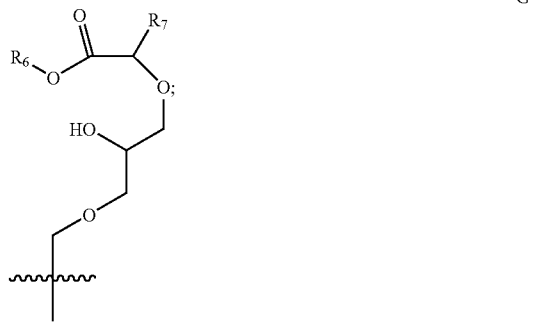
$G^6$ and

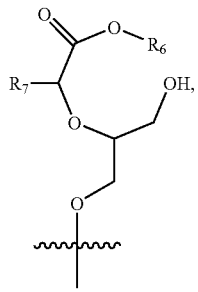
$G^7$ wherein $R_6$ is hydrogen or $C_{1-4}$ alkyl; and $R_7$ is selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl and phenyl ($C_{1-4}$)alkyl.

12. A composition comprising a moiety selected from the group consisting of a carboxyl moiety attached to a carbon chain that is 2 to 23 carbons in length, wherein the chain contains at least one dioxanone ring system and one or more sites of unsaturation; an ester moiety attached to a carbon chain that is 2 to 23 carbons in length, wherein the chain contains at least one dioxanone ring system and one or more sites of unsaturation; and, a polyester containing at least two ester moieties each of which is attached to a separate carbon chain that is 2 to 23 carbons in length, wherein at least one of said chains contains at least one dioxanone ring system and one or more sites of unsaturation; said dioxanone being formed from two adjacent carbons in the chain and having the following general structure (I):

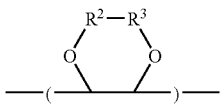

I wherein one of $R^2$ and $R^3$ is a carbonyl and the other of $R^2$ and $R^3$ is $CR_4R_5$, and wherein $R_4$ and $R_5$ are independently selected from the group consisting of hydrogen, $C_{1-10}$ alkyl, $C_{1-10}$ alkoxy, $C_{6-10}$ aryl, hydroxy, heteroaryl, $C_{3-6}$ cycloalkyl and phenyl($C_{1-4}$)alkyl, wherein the moieties comprise a fatty acid residue containing at least one dioxanone ring system, wherein said residue is obtained from an animal oil, fish oil, a vegetable oil, a genetically-modified vegetable oil, a chemically-modified vegetable oil or enzymatically-modified vegetable oil, copolymer oil, or mixtures or derivatives thereof.

13. A coating composition comprising a latex resin and the fatty acid residue of claim 12.

14. A polymer composition comprising the fatty acid residue of claim 12 and a diamine, wherein said polymer is formed by combining said fatty acid derivative and said diamine.

15. A polymer composition comprising the fatty acid residue of claim 12, wherein at least one said dioxanone ring system has been combined with a polyethylene glycol to form said polymer composition.

16. The composition of claim 11, wherein said unsaturated carbon chain contains 16 to 18 carbons.

* * * * *